United States Patent [19]

Chu

[11] 4,417,084
[45] Nov. 22, 1983

[54] PREVENTION OF POLYMER FORMATION IN DEHYDROGENATION OF P-ETHYLTOLUENE

[75] Inventor: Chin-Chiun Chu, North Brunswick, N.J.

[73] Assignee: Mobil Oil Corporation, New York, N.Y.

[21] Appl. No.: 126,247

[22] Filed: Mar. 3, 1980

[51] Int. Cl.³ .................................................. C07C 7/00
[52] U.S. Cl. .................................... 585/440; 585/442; 585/2; 585/950
[58] Field of Search ..................... 585/440, 950, 442, 2

[56] References Cited

U.S. PATENT DOCUMENTS 2,407,861  9/1946  Wolk ....................................... 203/9
3,585,250  6/1971  Pasternak et al. ................... 585/442

FOREIGN PATENT DOCUMENTS 594343  3/1960  Canada ................................ 585/440

Primary Examiner—Charles F. Warren
Assistant Examiner—Joseph A. Boska
Attorney, Agent, or Firm—A. J. McKillop; J. F. Powers, Jr.; E. F. Kenehan, Jr.

[57] ABSTRACT

In the catalytic dehydrogenation of p-ethyltoluene to p-methylstyrene, popcorn polymer forms and builds up in the condenser, shortly plugging it. This is prevented by adding minor amounts of $H_2S$ continuously to the gaseous product effluent entering the condenser.

1 Claim, No Drawings

PREVENTION OF POLYMER FORMATION IN DEHYDROGENATION OF P-ETHYLTOLUENE

BACKGROUND OF THE INVENTION

1. Field of the Invention

This invention is concerned with the catalytic dehydrogenation of p-ethyltoluene to p-methylstyrene. It is more particularly concerned with the prevention of polymer formation by the effluent gases in the condenser or cooling train.

2. Description of the Prior Art

It has been proposed to inhibit polymerization by adding various materials to vinyl aromatics being purified by distillation. Typical additives include nitrosoanilines, nitro and halo nitro substituted cresols, and halo nitrotoluene. Note, for example, U.S. Pat. Nos. 4,050,993; 4,086,147; 4,132,602; and 4,132,603. Insofar as is now known, it has not been proposed to prevent polymer formation in the cooling train by adding $H_2S$ to the effluent from the catalytic dehydrogenation of p-ethyltoluene.

SUMMARY OF THE INVENTION

This invention provides, in the method for dehydrogenating p-ethyltoluene to p-methylstyrene in the presence of steam at 550°–700° C. by passing a mixture of steam and p-ethyltoluene over a self-regenerative steam dehydrogenation catalyst, the improvement that comprises inhibiting formation of popcorn polymer in the cooling train by continuously adding a minor amount of $H_2S$ to the dehydrogenation effluent entering the cooling train.

DESCRIPTION OF SPECIFIC EMBODIMENTS

The dehydrogenation of ethylbenzenes is carried out in the vapor phase at elevated temperatures. In the case of the dehydrogenation of p-ethyltoluene, the hot effluent contains p-methylstyrene which forms a polymer, popcorn like in appearance, that builds up and clogs the condenser and other parts of the cooling train. In accordance with this invention, it has been found that this polymer formation is virtually completely eliminated by continuously adding a minor amount of $H_2S$ to the dehydrogenation effluent entering the cooling train.

The feed to the dehydrogenation is an ethylbenzene isomer mixture consisting essentially of about 90 to about 99 weight percent of the para isomer and about 1 to about 10 weight percent of the meta isomer and which is substantially free of the undesirable ortho isomer, usually less than 0.1 weight percent. Such mixtures and their preparation are fully described in U.S. Pat. Nos. 4,086,287 and 4,143,084, which are incorporated herein in their entirety by reference.

The catalysts utilizable in the steam dehydrogenation of alkyl aromatics to the corresponding vinyl aromatics are the self-regenerative steam dehydrogenation catalysts well known in the art. Some have been based primarily on ferric oxide or copper chromite with potassium added, usually in the form of potassium carbonate, to promote the water-gas reaction and thereby the catalyst from being choked with deposited catalyst. Representative prior art showing such catalysts includes U.S. Pat. Nos. 2,870,228; 2,916,531; 3,179,706; and 3,703,593 to which reference is made.

Other catalysts of this general type are based upon a mixture of ferric oxide and zinc oxide. Typically they are described in U.S. Pat. Nos. 3,205,179 and 3,907,916 to which reference is made. In another embodiment, the ferric oxide can be in the form of a mixture of yellow (hydrated) and red (dehydrated) ferric oxides, such as described in U.S. Pat. No. 3,703,593 to which reference is made.

In general, water in the form of steam is admixed with vaporized ethyltoluene in a steam to ethyltoluene weight ratio of between about 1.5 and about 4. The ethyltoluene is fed at a liquid hourly spaced velocity (LHSV) of between about 0.2 and about 3. The dehydrogenation reaction is feasibly carried out semi-continuously or continuously, using a fixed bed of self-regenerative steam dehydrogenation catalyst. The dehydrogenation reaction is carried out at temperature between about 550° C. and about 700° C.

The dehydrogenation reaction produces a methylstyrene isomer mixture having an isomer distribution corresponding to that of the feed, i.e., about 90 to about 99 weight percent of the para isomer and about 1 to about 10 percent of the meta isomer and which is substantially free of the undesirable ortho isomer, usually less than 0.1 weight percent. Because of the predominance of the para isomer, the mixture is conveniently called p-methylstyrene. The effluent also contains unreacted feed, which can be recycled, and water. As indicated hereinbefore, the hot p-methylstyrene in the effluent forms a popcorn polymer which clogs the condenser and other parts of the cooling train.

According to this invention, such popcorn polymer formation is virtually completely eliminated by continuously adding a minor amount of $H_2S$ to the dehydrogenation effluent entering the cooling train. Generally, the amount of $H_2S$ added will be between about 0.5 cc. and about 8 cc. per minute for 100 cc. per hour of p-ethyltoluene.

EXAMPLE 1

Into a reaction tube provided with means for feeding a vaporized mixture of steam and hydrocarbon and with a condenser and product recovery means, there was placed 100 cc. of a $Fe_2O_3$—$K_2CO_3$—$Cr_2O_3$ catalyst bed (76 wt. % $Fe_2O_3$, 20 wt. % $K_2CO_3$, 4 wt. % $Cr_2O_3$). A mixture of steam and hydrocarbon (97 wt. % p-ethyltoluene, 3 wt. % m-ethyltoluene) was continuously fed at an LHSV of water of 1.6 and an LHSV of hydrocarbon of 1.0. The catalyst bed temperature was 620° C. After several hours of operation, the condenser plugged up, due to formation and build-up of popcorn polymer. Before the condenser plugged, conversion was 72% and selectivity was 87.5%.

EXAMPLE 2

The run described in Example 1 was repeated, except that $H_2S$ was introduced continuously at a rate of 1 cc. per minute into the dehydrogenation effluent as it entered the condenser. There was no plugging of the condenser by popcorn polymer formation.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. In the method for dehydrogenating p-ethyltoluene to p-methylstyrene in the presence of steam at 550°–700° C. by passing a mixture of steam and p-ethyltoluene over a self-regenerative steam dehydrogenation catalyst, the improvement that comprises inhibiting formation of popcorn polymer in the cooling train by continuously adding a minor amount of $H_2S$ to the dehydrogenation effluent entering the cooling train.

* * * * *